US00PP27379P2

(12) United States Plant Patent
Pan

(10) Patent No.: US PP27,379 P2
(45) Date of Patent: Nov. 15, 2016

(54) ***LANTANA* PLANT NAMED 'LANZ0009'**

(50) Latin Name: ***Lantana camara* L.**
Varietal Denomination: LANZ0009

(71) Applicant: SYNGENTA PARTICIPATIONS AG, Basel (CH)

(72) Inventor: Shifeng Pan, Gilroy, CA (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/756,579

(22) Filed: Sep. 18, 2015

(51) Int. Cl.
*A01H 5/02* (2006.01)

(52) U.S. Cl.
USPC ..... Plt./227

(58) Field of Classification Search
USPC ..... Plt./227
CPC ..... A01H 5/02
See application file for complete search history.

*Primary Examiner* — Kent L Bell
(74) *Attorney, Agent, or Firm* — Joshua L. Price

(57) ABSTRACT

A new *Lantana* plant named 'LANZ0009' particularly distinguished by large size deep red and yellow flowers with free and early flowering, excellent inflorescences, down spreading plant habit and small size dark green foliage.

1 Drawing Sheet

Latin name of the genus and species of the plant claimed: *Lantana camara* L.

Varietal denomination: 'LANZ0009'.

BACKGROUND OF THE NEW PLANT

The present invention comprises a new *Lantana*, botanically known as *Lantana camara* and hereinafter referred to by the variety name 'LANZ0009'.

'LANZ0009' is a product of a planned breeding program. The new cultivar has large size deep red and yellow flowers with free and early flowering, excellent inflorescences, down spreading plant habit and small size, dark green foliage.

'LANZ0009' originates from the cross-pollination between Lucky Red Hot Improved and '103-5' made in July 2006 in a controlled breeding program in Gilroy, Calif., USA. The female parent was the commercial variety Lucky Red Hot Improved, 'Balucrehot', U.S. Plant Pat. No. 16,535, with red to yellow flowers, early and compact plant habit. The male parent was the unpatented, proprietary line designated '103-5', having orange color flowers and trailing plant habit.

The resulting seeds were sown in June 2007 in a greenhouse in Gilroy, Calif., USA and 'LANZ0009' was selected as one flowering plant within the progeny of the stated cross in November 2007.

The first act of asexual reproduction of 'LANZ0009' was accomplished when vegetative cuttings were propagated from the initial selection in December 2007 in a controlled environment in Gilroy, Calif.

BRIEF SUMMARY OF INVENTION

Horticultural examination of plants grown from cuttings of the plant initiated in spring of 2008 in Gilroy, Calif., and continuing thereafter, has demonstrated that the combination of characteristics as herein disclosed for 'LANZ0009' are firmly fixed and are retained through successive generations of asexual reproduction.

'LANZ0009' has not been observed under all possible environmental conditions. The phenotype may vary significantly with variations in environment such as temperature, light intensity, and day length.

Plant Breeder's Rights for this cultivar were not yet applied for.

The following traits have been repeatedly observed and are determined to be basic characteristics of the new variety. The combination of these characteristics distinguishes this *Lantana* as a new and distinct variety.

BRIEF DESCRIPTION OF THE PHOTOGRAPHS

The accompanying photographic drawings show typical flower and foliage characteristics of 'LANZ0009' with colors being as true as possible with an illustration of this type.

Figure 1:
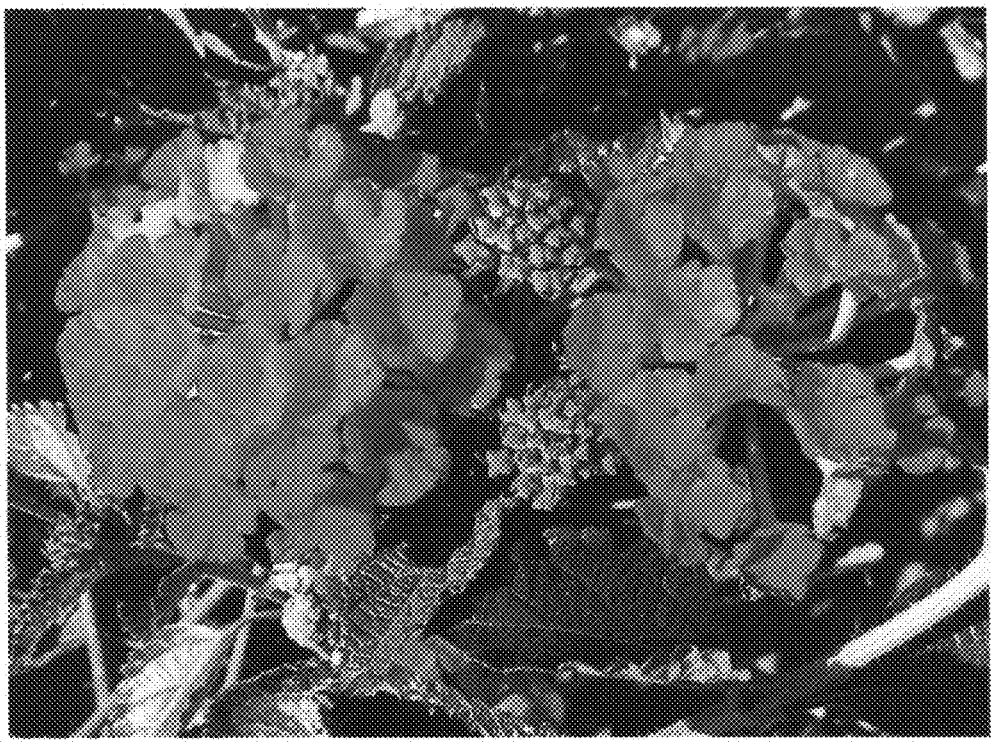
Figure 2:
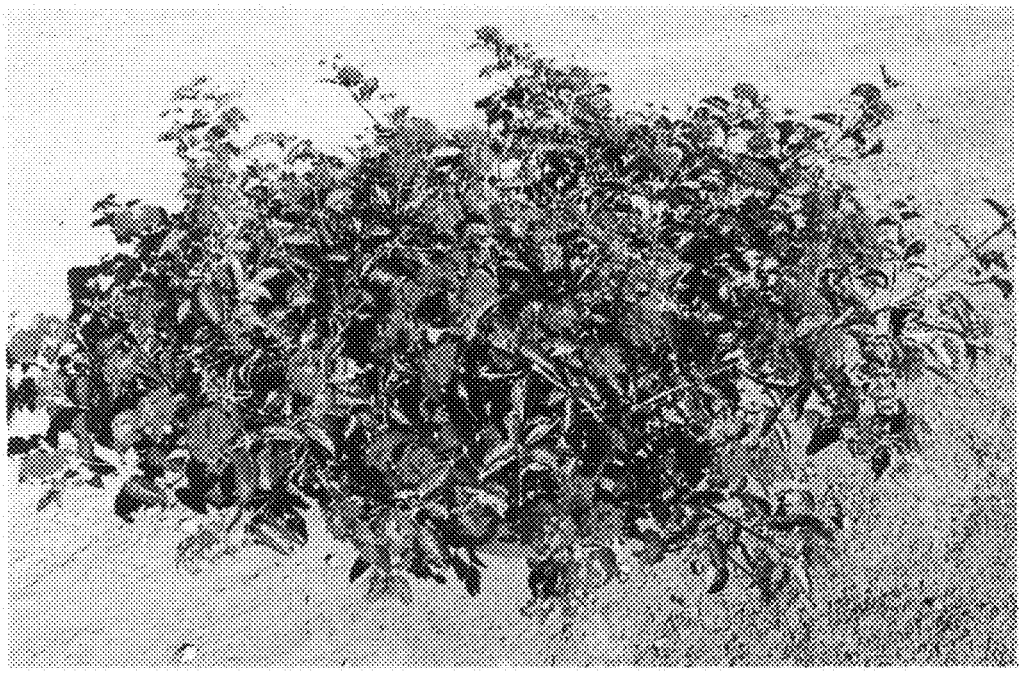

The photographic drawings show in FIG. 1, a close-up of the flowers and in FIG. 2, a flowering potted plant of the new variety.

DETAILED BOTANICAL DESCRIPTION

The aforementioned photographs were taken on August 12 in Gilroy, Calif. The plants were growing in 14 inch pots outdoors. They were about 18 weeks of age.

The plant descriptions and measurements were taken Gilroy, Calif. in August 2015. The plants were approximately 20 weeks old and were growing in 14 inch pots in an outdoor trial.

TABLE 1

DIFFERENCES BETWEEN THE NEW VARIETY 'LANZ0009' AND A SIMILAR VARIETY

| | 'LANZ0009' | 'BALANDLAE', U.S. Plant Pat. No. 190,028, commercially known as 'Landmark Blaze' |
|---|---|---|
| Overall flower color: | Red to yellow | Deeper red to yellow |
| Plant size: | 36-42 inch tall | Shorter 30-40 inch |
| Leaf size: | Smaller | Bigger |

Plant:

*Form, growth and habit.*—Semi-woody, grown as an annual or perennial; spreading habit; well branched.

*Plant height.*—91.5-106.7 cm.

*Plant height* (*inflorescence included*).—83.5-98.5 cm.

*Plant width.*—101.5-111.8 cm.

Foliage:

*Type.*—Opposite.

*Immature, leaf color, upper surface.*—Closest to RHS 139A.

*Lower surface.*—Closest to RHS 137B.

*Mature, leaf color, upper surface.*—Closest to RHS 139A.

*Lower surface.*—Closest to RHS 137B.

*Length.*—4.8-5.5 cm.

*Width.*—3.0-3.5 cm.

*Shape.*—Elliptic.

*Base shape.*—Rounded.

*Apex shape.*—Acute.

*Margin.*—Dentate.

*Texture, upper.*—Hirsute.

*Lower surface.*—Hirsute.

*Lower surface.*—RHS 137B.

*Pattern of veining.*—Pinnate.

*Petioles color.*—RHS 147B.

*Petioles length.*—0.8-1.2 cm.

*Diameter of petiole.*—0.1-0.2 cm.

*Texture* (*upper and lower surface*).—Hirsute with some very short glandular hairs.

Stem:

*Color of stem.*—RHS 146C.

*Length of stem.*—About 14.0 cm.

*Diameter.*—0.50 cm.

*Length of internodes.*—4.3-5.0 cm.

*Texture.*—Pilose, hirsute.

Inflorescence:

*Type.*—Umbel like, flattened semi-sphere the florets are sessile on an ovate receptacle.

*Blooming habit.*—Flowers continuously from spring through fall.

*Number of open flowers per inflorescence.*—31-35.

*Quantity of inflorescences per plant.*—About 180 (with open florets).

*Lastingness of individual blooms on the plant.*—About 4 weeks (depending on temperatures).

*Fragrance.*—Slightly spicy.

*Umbel horizontal diameter.*—About 3.2 cm.

*Umbel vertical height.*—1.9-2.2 cm.

*Peduncle color.*—RHS 146B.

*Length of peduncle.*—2.8-3.8 cm.

*Peduncle diameter.*—0.2 cm.

*Texture.*—Hirsute, glandular hairs.

Flower:

*Floret form.*—Corolla salver-shaped to shallow cup-shaped, with a relatively long tube at the base; each flower subtended by a single bract.

*Length of floret.*—1.2-1.8 cm.

*Width of floret.*—0.9-1.2 cm.

*Depth of floret.*—0.9-1.2 cm.

*Young floret, color upper surface.*—RHS 46A.

*Young floret, color lower surface.*—RHS 54A.

*Mature florets, color upper surface.*—RHS 45A to RHS 15A.

*Mature floret, color lower surface.*—RHS 161D overlain with RHS 175A.

*Apex shape.*—Rounded.

*Degree of lobation.*—Moderate.

*Margin.*—Crenate.

*Base.*—Fused.

*Texture, upper surface.*—Papillose.

*Lower surface.*—Papillose.

*Tube, color outer surface.*—Closest to RHS 178B.

*Tube, color inner surface.*—Closest to RHS 161A.

*Tube, length.*—1.3 cm.

*Tube, diameter* (*at opening*).—0.17 cm.

*Tube, texture outer surface.*—Pubescent.

*Inner surface.*—Hirsute.

Bud (just before opening):

*Color.*—RHS 46A.

*Length:* 0.3-0.5 cm.

*Width.*—0.2-0.4 cm at the apex.

*Shape.*—Tubular with a flared apex.

Bract:

*Color.*—Closest to RHS 147B.

*Length.*—0.6-0.8 cm.

*Diameter.*—0.15-0.2 cm.

*Texture, upper surface.*—Hirsute.

*Lower surface.*—Hirsute.

Calyx:

*Number of sepals.*—5, fused sepals forming a short tube around the base of the floret.

*Color of sepals.*—RHS 148C.

*Length of sepals.*—0.3 cm.

*Width of sepals.*—0.15 cm.

*Apex shape.*—Acuminate.

*Margins.*—Entire.

*Texture, outer surface.*—Pubescent.

*Inner surface.*—Glabrous.

Reproductive organs:

*Gynoecium.*—Pistil quantity: One. Length: 0.4 cm. Style color: RHS 161A. Style length: 0.25 cm. Stigma color: RHS 147C. Ovary color: RHS 148B. Ovary length: 0.1 cm. Ovary diameter: 0.1 cm.

*Androecium.*—Stamen quantity: 4. Color of filaments: RHS 161A. Length filaments: 0.6-0.7 cm. Anther color: RHS 165B. Length of anthers: 0.1 cm. Color of pollen: RHS 165A. Pollen amount: Normal.

Fertility/seed set: Has not been determined to date.

Disease/pest resistance: Has not been determined to date.

What is claimed is:

1. A new and distinct variety of *Lantana* plant named 'LANZ0009', substantially as illustrated and described herein.

* * * * *